United States Patent [19]

Sasaki et al.

[11] Patent Number: 5,468,721

[45] Date of Patent: Nov. 21, 1995

[54] PHENOXYMETHYLPYRIMIDINE DERIVATIVE AND USE THEREOF AS HERBICIDE

[75] Inventors: Norio Sasaki; Sachio Kudo; Michi Watanabe; Keiji Endo; Shinji Kawaguchi, all of Ami, Japan

[73] Assignee: Mitsubishi Petrochemical Co., Ltd., Tokyo, Japan

[21] Appl. No.: 140,062

[22] PCT Filed: Apr. 28, 1992

[86] PCT No.: PCT/JP92/00560

§ 371 Date: Oct. 29, 1993

§ 102(e) Date: Oct. 29, 1993

[87] PCT Pub. No.: WO92/19603

PCT Pub. Date: Dec. 11, 1992

[30] Foreign Application Priority Data

Apr. 30, 1991 [JP] Japan .................... 3-098511

[51] Int. Cl.$^6$ .................... C07D 239/52; A01N 43/54
[52] U.S. Cl. .................... 504/243; 544/296; 544/319
[58] Field of Search .................... 544/319, 296; 504/243

[56] References Cited

U.S. PATENT DOCUMENTS

| 377,371 | 5/1982 | Levitt | 544/211 |
|---|---|---|---|
| 472,879 | 3/1983 | Levitt | 544/211 |
| 4,496,392 | 1/1985 | Levitt | 544/211 |

FOREIGN PATENT DOCUMENTS

| PO0012 | 5/1977 | Australia . |
| 0223406 | 5/1987 | European Pat. Off. . |
| 0249708 | 12/1987 | European Pat. Off. . |
| 53-137979 | 12/1978 | Japan . |
| 54-117486 | 4/1979 | Japan . |
| 54-55729 | 5/1979 | Japan . |
| 54-92978 | 7/1979 | Japan . |
| 58-206572 | 12/1983 | Japan . |
| 62-174059 | 7/1987 | Japan . |
| 62-502901 | 11/1987 | Japan . |
| 63-115870 | 5/1988 | Japan . |
| 63-258463 | 10/1988 | Japan . |

Primary Examiner—John M. Ford
Attorney, Agent, or Firm—Wenderoth, Lind & Ponack

[57] ABSTRACT

A phenoxymethylpyrimidine derivative represented by the general formula (1)

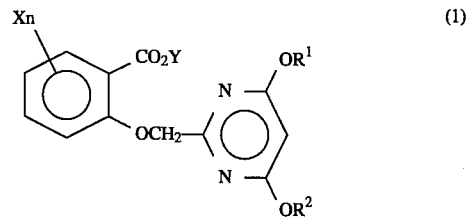

and a herbicide containing it as an effective ingredient. This compound has a high weed killing effect, a wide weed killing spectrum and high safety on crops, and is thus useful as a herbicide.
wherein X denotes a halogen atom, a lower alkyl group, a lower alkoxy group, a lower acyloxy group or a nitro group, n denotes an integer of 0, 1 or 2, Y denotes a hydrogen atom, a lower alkyl group, a lower alkenyl group, a lower alkynyl group, a substituted lower alkyl group, a substituted lower alkenyl group, a substituted lower alkynyl group, an alkali metal atom, an alkaline earth metal atom or an ammonium cation optionally substituted by alkyl group(s), and $R^1$ and $R^2$ each independently denote a lower alkyl group.

11 Claims, No Drawings

PHENOXYMETHYLPYRIMIDINE DERIVATIVE AND USE THEREOF AS HERBICIDE

TECHNICAL FIELD

This invention relates to a novel phenoxymethylpyrimidine derivative and the utilization thereof as a herbicide. More detailedly, this invention relates to a novel phenoxymethylpyrimidine derivative having such structure that a phenyl group having a specific substituent binds to the 2-position of a 4,6-di-lower alkoxypyrimidine through an oxygen atom and a methylene group, a herbicide containing it as an effective ingredient, and a method for the control or weed killing of weeds comprising applying the herbicide onto a piece of agricultural land.

BACKGROUND ART

Heretofore, many proposals have been made over many years about compounds having a phenoxypyrimidine skeleton and the utilization thereof as a herbicide. Representative literatures thereon are introduced below.

(1) Japanese Laid-Open Patent Publication No. 92978/1979

The following phenoxypyrimidine derivatives are disclosed as representative examples in this publication.

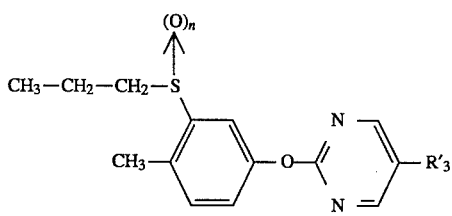

wherein $R'_3$ denotes a halogen atom.

It is disclosed in this publication that the above compounds have a miticidal action, but there is no suggestion about a herbicidal action.

(2) Japanese Laid-Open Patent Publication No. 117486/1979

In this publication, the following substituted phenoxypyrimidine derivatives are disclosed and suggested to have a herbicidal activity, but specific herbicidal activities are not disclosed at all.

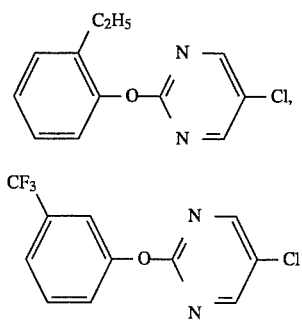

(3) Japanese Laid-Open Patent Publication No. 55729/1979

In this publication, the following phenoxypyrimidine derivatives having a herbicidal activity are, for example, disclosed.

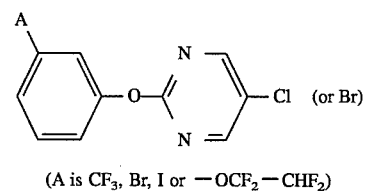

(A is $CF_3$, Br, I or $-OCF_2-CHF_2$)

(4) Japanese Laid-Open Patent Publication No. 174059/1987

In this publication, a pyrimidine derivative represented by the following general formula and a herbicide containing it as an effective ingredient are disclosed.

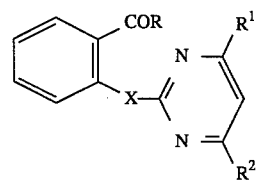

wherein X denotes O or S.

(5) Japanese Laid-Open Patent Publication No. 115870/1988

In this publication, a 2-phenoxypyrimidine derivative represented by the following general formula and a herbicide containing it as an effective ingredient are disclosed.

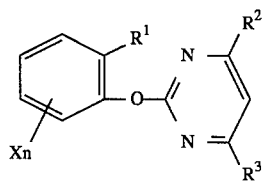

PROBLEMS TO BE SOLVED BY THE INVENTION

However, compounds disclosed in the above literatures do not necessarily have satisfactory performance in practical viewpoints on aspects such as weed killing spectrum, the amount thereof to be applied and crop selectivity, and the development of further excellent herbicides is desired.

The present inventors intensely studied for development of a herbicide having a wide weed killing spectrum and a high herbicidal effect and excellent in safety on crops, and as a result they found that phenoxymethylpyrimidine derivatives having such specific structure that a phenyl group binds to the 2-position of a di-lower alkoxypyrimidine through an oxygen atom and a methylene group exhibit an excellent herbicidal effect on not only annual but perennial weeds and, in addition, have high safety on crops, and completed this invention.

MEANS FOR SOLVING THE PROBLEMS

There is provided according to this invention a phenoxymethylpyrimidine derivative represented by the following general formula (1)

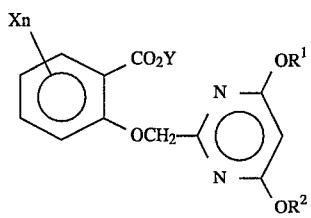

(1)

wherein

X denotes a halogen atom, a lower alkyl group, a lower alkoxy group, a lower acyloxy group or a nitro group, n denotes an integer of 0, 1 or 2, Y denotes a hydrogen atom, a lower alkyl group, a lower alkenyl group, a lower alkynyl group, a substituted lower alkyl group, a substituted lower alkenyl group, a substituted lower alkynyl group, an alkali metal atom, an alkaline earth metal atom or an ammonium cation optionally substituted by alkyl group(s), and $R^1$ and $R^2$ each independently denote a lower alkyl group.

In the definition of X, Y, $R^1$ and $R^2$ in the above general formula (1), specific examples of each group and atom are mentioned below.

Halogen atom:

For example, fluorine, chlorine, bromine, iodine, etc.

Lower alkyl group:

For example, lower alkyl groups having 4 or less carbon atoms such as methyl, ethyl, n-propyl, isopropyl, n-butyl, sec-butyl and text-butyl groups; etc.

Lower alkoxy group:

For example, lower alkoxy groups having 4 or less carbon atoms such as methoxy, ethoxy, n-propoxy, isopropoxy, n-butoxy, sec-butoxy and tert-butoxy groups; etc.

Lower acyloxy group:

For example, lower acyloxy groups having 4 or less carbon atoms such as acetyloxy and propionyloxy groups.

Lower alkenyl group:

For example, lower alkenyl groups having 4 or less carbon atoms such as vinyl, allyl, 3-butenyl and 1-methyl-2-propenyl groups.

Lower alkynyl group:

For example, propargyl, 2-butynyl, 3-butynyl, etc.

Lower alkylthio group:

For example, lower alkylthio groups having 4 or less carbon atoms such as methylthio, ethylthio, n-propylthio, isopropylthio, n-butylthio, sec-butylthio and tert-butylthio.

Optionally substituted phenyl group:

Phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2,4-dichlorophenyl and 2,4-dimethylphenyl groups, etc.

Optionally substituted heterocyclic group:

For example, pyridyl, thienyl, furyl, pyrimidyl, pyrazolyl, imidazolyl, triazolyl and thiazolyl groups are mentioned, and as their substituents halogens and lower alkyl, lower alkoxy and lower alkylthio groups, etc. are mentioned.

Alkali metal atom:

For example, sodium, potassium, etc.

Alkaline earth metal atom:

For example, calcium, barium, etc.

Ammonium cation optionally substituted by alkyl group(s)

For example, ammonium, methylammonium, dimethylammonium, trimethylammonium, ethylammonium, diethylammonium, triethylammonium, propylammonium and diisopropylammonium groups, etc.

Although, in the above general formula (1), X denotes a halogen atom, a lower alkyl group, a lower alkoxy group, a lower acyloxy group or a nitro group, and n denotes 0, 1 or 2, it is preferable, among them, that X is a halogen atom, a lower alkyl group or a lower alkoxy group and the most preferable is the case where X is a halogen atom, a methyl group or a methoxy group and n is 1. Further, when n is 1, the 6-position is the most preferable as the bond position of Xn on the benzene ring.

Y denotes a hydrogen atom, a lower alkyl group, a lower alkenyl group, a lower alkynyl group, a substituted lower alkyl group, a substituted lower alkenyl group, a substituted lower alkynyl group, an alkali metal atom, an alkaline earth metal atom or an ammonium cation optionally substituted by alkyl group(s), and as the substituent of the substituted lower alkyl group, the substituted lower alkenyl group and the substituted lower alkynyl group, there can be mentioned a halogen atom, a lower alkoxy group, a lower alkylthio group, a carboxyl group, a carboxyalkyl group, an optionally substituted phenyl group or an optionally substituted heterocyclic group. Preferable as the above Y is a hydrogen atom, a sodium atom, a lower alkyl group or an optionally alkyl-substituted ammonium cation (a lower alkyl group is suitable as the alkyl of the "alkyl-substituted"). Particularly preferable among them is a hydrogen atom, a methyl group, an ethyl group, an ammonium cation or an alkyl-substituted ammonium cation.

Although $R^1$ and $R^2$ each independently denote a lower alkyl group, the most preferable is the case where both $R^1$ and $R^2$ are methyl groups.

There are shown in Table 1 examples of the compounds of this invention represented by the above general formula (1).

TABLE 1

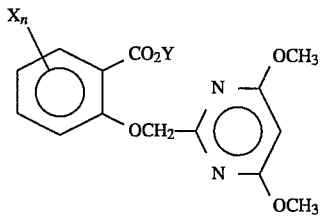

| Compound No. | Xn | Y |
|---|---|---|
| 1 | — | H |
| 2 | — | $CH_3$ |
| 3 | — | $C_2H_5$ |
| 4 | — | $CH_2CH_2OCH_3$ |
| 5 | — | $NH_4$ |
| 6 | 3-Cl | H |
| 7 | 3-Cl | $CH_3$ |
| 8 | 3-Cl | $C_2H_5$ |
| 9 | 3-Cl | iso-$C_3H_7$ |
| 10 | 3-Cl | $CH_2CH=CH_2$ |
| 11 | 4-Cl | H |
| 12 | 4-Cl | $CH_3$ |
| 13 | 4-Cl | $C_2H_5$ |
| 14 | 4-Cl | n-$C_4H_9$ |
| 15 | 4-Cl | $CH_2-\text{\textlangle{}phenyl\textrangle{}}$ |
| 16 | 5-Cl | H |
| 17 | 5-Cl | $CH_3$ |
| 18 | 5-Cl | $C_2H_5$ |
| 19 | 5-Cl | iso-$C_3H_7$ |
| 20 | 5-Cl | $CH_2CO_2CH_3$ |

TABLE 1-continued

Structure: Xn-phenyl(CO₂Y)(OCH₂-pyrimidine with 4,6-diOCH₃)

| Compound No. | Xn | Y |
|---|---|---|
| 21 | 5-Cl | $CH_2C{\equiv}CH$ |
| 22 | 6-Cl | H |
| 23 | 6-Cl | $CH_3$ |
| 24 | 6-Cl | $C_2H_5$ |
| 25 | 6-Cl | $n\text{-}C_3H_7$ |
| 26 | 6-Cl | $iso\text{-}C_3H_7$ |
| 27 | 6-Cl | $n\text{-}C_4H_9$ |
| 28 | 6-Cl | $CH_2CH{=}CH_2$ |
| 29 | 6-Cl | $CH_2CH{\equiv}CH$ |
| 30 | 6-Cl | $CH_2CH_2Cl$ |
| 31 | 6-Cl | $CH_2$–phenyl |
| 32 | 6-Cl | Na |
| 33 | 6-Cl | $NH_4$ |
| 34 | 6-Cl | $CH_2$–(4,6-dimethoxypyrimidin-2-yl) |
| 35 | — | $CH_2$–(4,6-dimethoxypyrimidin-2-yl) |
| 36 | 3,6-Cl₂ | H |
| 37 | 3,6-Cl₂ | $CH_3$ |
| 38 | 3,6-Cl₂ | $CH_2OCH_2$–phenyl |
| 39 | 3,6-Cl₂ | $CH_2CH_2OCH_3$ |
| 40 | 3,6-Cl₂ | $CH_2CH_2OC_2H_5$ |
| 41 | 3,6-Cl₂ | $CH_2CO_2CH_3$ |
| 42 | 3,6-Cl₂ | $CH(CH_3)CO_2C_2H_5$ |
| 43 | 3,6-Cl₂ | $CH_2OC_2H_5$ |
| 44 | 6-$CH_3$ | H |
| 45 | 6-$CH_3$ | $CH_3$ |
| 46 | 6-$CH_3$ | $C_2H_5$ |
| 47 | 6-$CH_3$ | $CH_2CH_2Cl$ |
| 48 | 6-$CH_3$ | $CH_2OC_2H_5$ |
| 49 | 6-$OCH_3$ | H |
| 50 | 6-$OCH_3$ | $CH_3$ |
| 51 | 6-$OCH_3$ | $CH_2CH{=}CH_2$ |
| 52 | 6-$OCH_3$ | $CH_2OC_2H_5$ |
| 53 | 6-$OCH_3$ | $CH_2$–(4,6-dimethoxypyrimidin-2-yl) |
| 54 | 6-Cl | $NH(C_2H_5)_3$ |
| 55 | 6-Cl | K |
| 56 | 6-Cl | ½Ca |
| 57 | 6-$OCOCH_3$ | $CH_3$ |
| 58 | 6-$OCOCH_3$ | $C_2H_5$ |
| 59 | 6-$OCOCH_3$ | $iso\text{-}C_3H_7$ |
| 60 | 4-$NO_2$ | H |
| 61 | 4-$NO_2$ | $CH_3$ |
| 62 | 4-$NO_2$ | $C_2H_5$ |
| 63 | — | $CH_2$–(4-methylphenyl) |
| 64 | — | $CH_2$–(thien-2-yl) |
| 65 | 6-Cl | $CH_2CO_2CH_3$ |
| 66 | 6-Cl | $CH_2OC_2H_5$ |
| 67 | 6-Cl | $CH_2CH_2F$ |
| 68 | 6-Cl | $CH_2$–(4-chlorophenyl) |
| 69 | 3-Cl | $CH(CH_3)CO_2C_2H_5$ |
| 70 | 3-Cl | $CH_2CH_2OC_2H_5$ |
| 71 | 3-Cl | $CH_2CO_2CH_3$ |
| 72 | 3-Cl | $CH_2$–(4,6-dimethoxypyrimidin-2-yl) |
| 73 | 6-Cl | $(CH_3)_2NH_2$ |
| 74 | 6-Cl | $n\text{-}C_8H_{17}NH_3$ |
| 75 | 6-Cl | $(C_2H_5)_2NH_2$ |

A compound (1) of this invention can, for example, be prepared according to the following process (Process A, Process B, Process C, Process D or Process E). These can appropriately be altered or appropriately be combined.

Process A

Synthetic route according to Process A

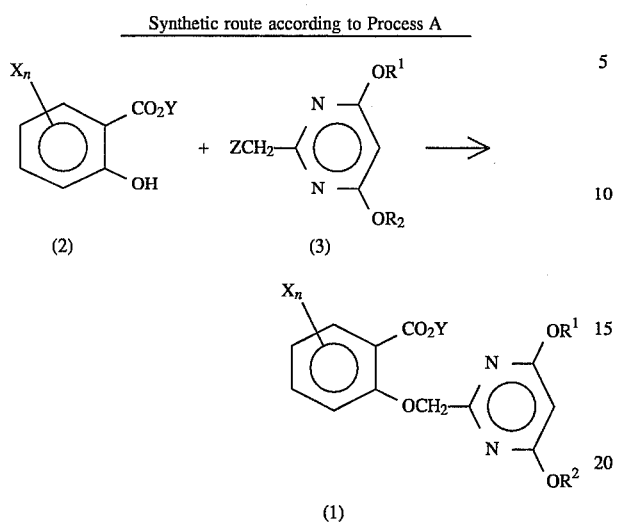

wherein X, n, Y, $R^1$ $R^2$ have the same meaning as defined above, and Z denotes a halogen atom or an alkylsufonyloxy group.

In the above reaction formula of Process A, the compound represented by the formula (1) can be prepared by reacting the salicylic acid derivative of the above formula (2) with the pyrimidine derivative of the above formula (3) using a suitable base in the absence of a solvent or in the presence of a suitable solvent in the temperature range of $-78°$ C. to the boiling point of the solvent for 1 to 24 hours.

The compound (3) as a raw material for this reaction can, for example, be synthesized according to Journal of Heterocyclic Chemistry, 26, 913.

When a solvent is used in this reaction, there can, for example, be mentioned as examples thereof hydrocarbonic solvents such as benzene, toluene and xylene; halogenated hydrocarbon solvents such as dichloromethane and chloroform; ethereal solvents such as diethyl ether, diisopropyl ether, tetrahydrofuran and 1,4-dioxane; ketonic solvents such as acetone and methyl ethyl ketone; ester solvents such as methyl acetate and ethyl acetate; aprotic polar solvents such as dimethylformamide, dimethylsulfoxide and dimethylacetamide; acetonitrile; water; etc.

Further, as bases, there can be mentioned carbonates such as sodium carbonate and potassium carbonate; metal hydroxides such as sodium hydroxide and potassium hydroxide; metal alcoholates such as sodium methylate and sodium ethylate; alkali metal hydrides such as sodium hydride and potassium hydride; lithium amides such as lithium diethyl amide, lithium diisopropyl amide and lithium bis(trimethylsilyl) amide.

Process B

Synthetic route according to Process B

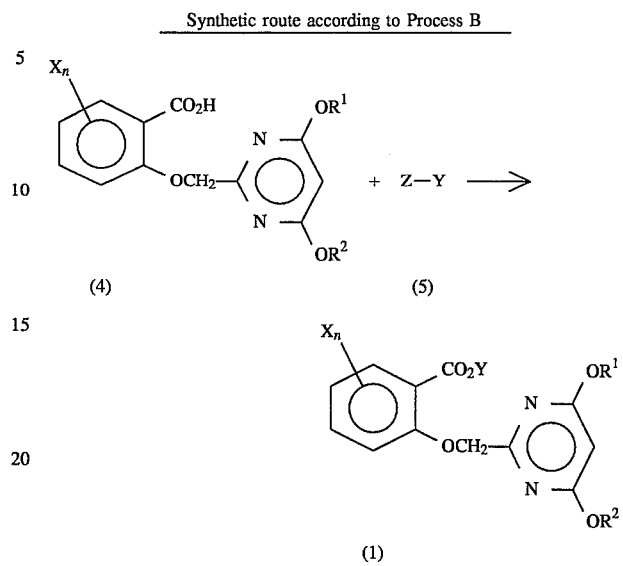

wherein n, Y, $R^1$ and $R^2$ have the same meanings as defined above, and Z denotes a hydroxyl group, a halogen atom, an alkylsulfonyloxy group (e.g., a methanesulfonyloxy group, an ethanesulfonyloxy group or the like) or an arylsulfonyloxy group (e.g., a benzensulfonyloxy group or a paratoluenesulfonyloxy group or the like).

A compound represented by the formula (1) in the above reaction formula can be prepared by reacting a carboxylic acid represented by the formula (4) with a compound represented by the formula (5) in the presence of a suitable condensing agent in the absence or presence of a suitable solvent in the temperature range of under ice cooling to the boiling point of the solvent for 1 to 48 hours.

As solvents used for the reaction, there can be mentioned hydrocarbonic solvents such as benzene, toluene and xylene; halogenated hydrocarbon solvents such as dichloromethane and chloroform; ethereal solvents such as diethyl ether, diisopropyl ether, tetrahydrofuran and 1,4-dioxane; ketonic solvents such as acetone and methyl ethyl ketone; ester solvents such as methyl acetate and ethyl acetate; aprotic polar solvents such as dimethylformamide, dimethylsulfoxide, dimethylacetamide and acetonitrile; etc.

Further as condensing agents, there can be mentioned carbonates such as sodium carbonate, potassium carbonate, sodium bicarbonate and potassium bicarbonate; metal hydroxides such as sodium hydroxide and potassium hydroxide; metal alcoholates such as sodium methylate and sodium ethylate; alkali metal hydrides such as sodium hydride and potassium hydride; organic bases such as diazabicycloundecene; dehydrating-condensing agents such as dicyclohexylcarbodiimide.

Synthetic route according to Process C

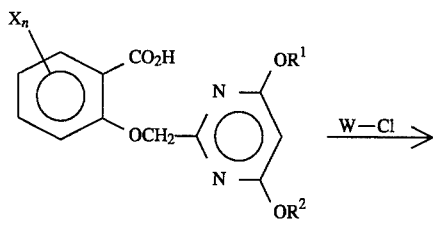

(4)

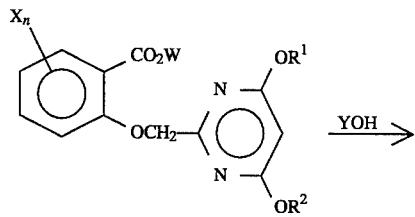

(6)

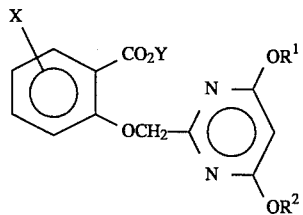

(1)

wherein X, n, Y, $R^1$ and $R^2$ have the same meanings as defined above, and W denotes a lower alkoxycarbonyl group, an optionally substituted aryloxycarbonyl group, a lower alkylsulfonyl group or an optionally substituted arylsulfonyl group.

In the above reaction formula, a compound represented by the formula (1) can be prepared by reacting a carboxylic acid of the formula (4) with a suitable activator represented by W-Cl in the presence of a suitable base to give an active intermediate represented by the formula (6), and then reacting the latter with a corresponding alcohol in the absence or presence of a catalyst.

As solvents used in the reaction, there can, for example, be mentioned hydrocarbonic solvents such as benzene, toluene and xylene; halogenated hydrocarbon solvents such as dichloromethane and chloroform; ethereal solvents such as diethyl ether, diisopropyl ether, tetrahydrofuran and 1,4-dioxane; ketonic solvents such as acetone and methyl ethyl ketone; ester solvents such as methyl acetate and ethyl acetate; aprotic polar solvents such as dimethylformamide, dimethylsulfoxide and dimethylacetamide; acetonitrile; water; etc.

As bases, there can be mentioned organic bases such as pyridine and triethylamine, and as activators, there can be mentioned alkyl chloroformates such as methyl chloroformate and ethyl chloroformate; aryl chloroformates such as phenyl chloroformate; alkylsulfonyl chlorides such as benzenesulfonyl chloride, methanesulfonyl chloride and ethanesulfonyl chloride; arylsulfonyl chlorides such as toluenesulfonyl chloride; etc. As catalysts, there can be mentioned dimethylaminopyridine, 4-pyrrolidinopyridine, etc.

Synthetic route according to Process D

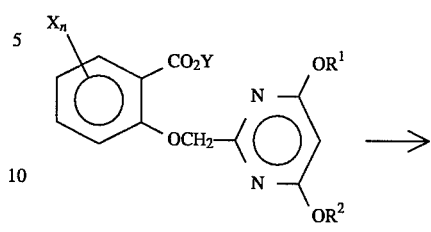

(1)

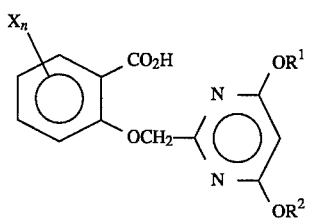

(4)

wherein X, n, Y, $R^1$ and $R^2$ have the same meanings as defined above.

A carboxylic acid represented by the formula (4) in the above reaction formula can be prepared by hydrolizing a compound represented by the formula (1) in the presence of an acid or a base in water or a mixture of water with a suitable solvent in the temperature range of under ice cooling to the boiling point of the solvent for 1 to 48 hours.

As solvents used in the reaction, there can be mentioned alcoholic solvents such as methanol, ethanol and isopropanol; hydrocarbonic solvents such as benzene and xylene; halogenous solvents such as dichloromethane, chloroform and dichloroethane; ethereal solvents such as diethyl ether, diisopropyl ether, tetrahydrofuran and 1,4-dioxane; ketonic solvents such as acetone and methyl ethyl ketone; aprotic polar solvents such as dimethylformamide, dimethylsulfoxide and acetonitrile; etc.

As acids, there can be mentioned inorganic acids such as hydrochloric acid, sulfuric acid and phosphoric acid; arylsulfonic acids such as benzenesulfonic acid and paratoluenesulfonic acid; and Lewis acids such as boron trifluoride and aluminum chloride, and as bases, there can be mentioned alkali metal hydroxides such as sodium hydroxide, potassium hydroxide and lithium hydroxide; alkaline earth metal hydroxides such as calcium hydroxide; etc.

Synthetic route according to Process E

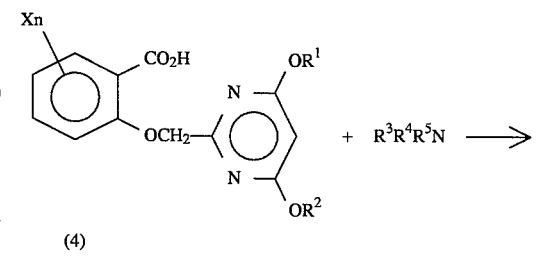

(4)

-continued
Synthetic route according to Process E

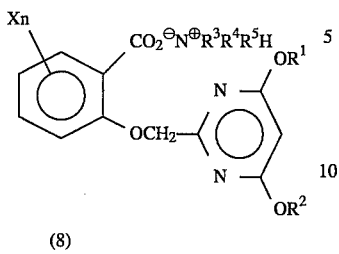

(8)

wherein n and X have the same meanings as defined above, and $R^3$, $R^4$ and $R^5$ each independently denote a hydrogen atom, an aforesaid lower alkyl group or an aforesaid substituted lower alkyl group.

In the above reaction formula, a carboxylate salt represented by the formula (8) can be prepared by reacting a carboxylic acid represented by the formula (4) with an amine represented by the formula (7) in the absence or presence of a solvent.

As solvents used in the reaction, there can be mentioned alcoholic solvents such as methanol, ethanol and isopropanol; hydrocarbonic solvents such as hexane, benzene, toluene and xylene; halogenated hydrocarbon solvents such as dichloroethane, chloroform, dichloroethane and carbon tetrachloride; ethereal solvents such as diethyl ether, diisopropyl ether, tetrahydrofuran and 1,4-dioxane; ketonic solvents such as acetone and methyl ethyl ketone; ethyl acetate; acetonitrile; water; etc.

As amines of the formula (7), there can be mentioned ammonia; alkylamines such as methylamine, dimethylamine, trimethylamine, ethylamine, diethylamine, triethylamine, isopropylamine, diisopropylamine, butylamine, isobutylamine, sec-butylamine, tertbutylamine, dibutylamine, amylamine, hexylamine, heptylamine, octylamine and nonylamine; aromatic amines such as aniline, N-methylaniline, N,N-dimethylaniline, N-ethylaniline and anisidine; etc.

The compounds of this invention are more specifically described below according to examples.

EXAMPLE 1

Synthesis of 2-[(4,6-dimethoxy-2-pyridyl)methyloxy] benzoate (Compound No. 2) (Process A)

1.52 g of methyl salicylate, 2.33 g of 2-bromomethyl-4, 6-dimethoxypyrimidine and 1.6 g of potassium carbonate were stirred in 20 ml of dimethylformamide at 60° C. for 2 hours. The reaction mixture was poured in ice water and extracted with ethyl acetate. The extract was dried over sodium sulfate and, after distilling off the solvent, purified using silica gel chromatography to obtain 2.5 g of methyl 2-(4,6-dimethoxy- 2-pyrimidyl)methyloxybenzoate (yield 82%).

Compound Nos. 7, 12, 17, 23, 29, 37, 43, 45, 48, 50, 52, 53, 57, 61, 66 and 77 shown in the above Table 1 were synthesized in the same manner as described above, changing raw materials for reaction.

The NMR spectra and/or melting points of these compounds are shown in Table 2. In the table, "—" means "unmeasured".

TABLE 2

| Compound No. | $^1$H-NMR (δ, in CDCl$_3$; ppm) | M.P. (°C.) |
|---|---|---|
| 2 | 3.9(9H, s), 5.23(2H, s), 5.93(1H, s), 6.8–7.9(4H, m) | — |
| 7 | — | — |
| 12 | 3.85(9H, s), 5.15(3H, s), 5.85(1H, s), 6.75–7.85(3H, m) | 82.5–83.0 |
| 17 | 3.87(9H, s), 5.18(2H, s), 5.90(1H, s), 6.85–7.81(3H, m) | 92.5–93.5 |
| 23 | 3.86(6H, s), 3.93(3H, s), 5.13(2H, s), 5.90(1H, s), 6.73–7.36(3H, m) | 124–126 |
| 29 | 2.36–2.53(1H, m), 3.83(6H, s), 4.83–4.93(1H, m), 5.10(2H, s), 5.83(1H, s), 6.63–7.33(3H, m) | — |
| 37 | 3.82(3H, s), 3.90(6H, s), 5.12(2H, s), 5.98(1H, s), 7.12(1H, d), 7.40(1H, d) | — |
| 43 | 1.18(3H, t), 3.71(2H, d), 3.90(6H, s), 5.13(2H, s), 5.43(2H, s), 5.95(1H, s), 7.10(1H, d), 7.38(1H, d) | — |
| 45 | 3.90(9H, s), 5.16(2H, s), 5.90(1H, s), 6.66–6.90(2H, m), 7.10–7.33(1H, m) | — |
| 48 | 1.16(3H, t), 2.33(3H, s), 3.76(2H, q), 3.86(6H, s), 5.10(2H, s), 5.50(2H, s), 5.90(1H, s), 6.60–6.90(2H, m), 7.10–7.30(1H, m) | — |
| 50 | 3.80(3H, s), 3.88(9H, s), 5.10(2H, s), 5.87(1H, s), 6.06–6.66(2H, m), 7.07–7.40(1H, m) | — |
| 52 | 1.20(3H, t), 3.70(2H, q), 3.78(3H, s), 3.86(6H, s), 5.06(2H, s), 5.43(2H, s), 5.83(1H, s), 6.16–6.66(2H, dd), 7.0–7.26(1H, m) | — |
| 53 | 3.80(3H, s), 3.85(6H, s), 3.90(9H, s), 5.13(2H, s), 5.33(2H, s), 5.90(2H, s), 6.58(2H, dd), 7.20–7.36(1H, m) | — |
| 57 | 2.23(3H, s), 3.87(9H, s), 5.18(2H, s) 5.92(1H, s), 6.6–7.53(3H, m) | 46–47 |
| 61 | — | 126–130 |
| 66 | 1.23(3H, t), 3.76(2H, q), 3.86(6H, s), 5.13(2H, s), 5.50(2H, s), 5.90(1H, s), 6.73–7.30(3H, d) | — |
| 72 | 3.83(6H, s), 3.90(9H, s), 5.13(2H, s), 5.36(2H, s), 5.90(2H, s), 6.76–7.30(3H, m) | — |

EXAMPLE 2

Synthesis of methoxycarbonylmethyl 3,6-dichloro-2-[ 4,6-dimethoxy-2-pyrimidyl)methyloxy]benzoate (Compound No. 41) (Process B)

1.18 g 3,6-dichloro-2-[(4,6-dimethoxy-2-pyrimidyl)methyloxy] benzoic acid, 0.3 g of methyl bromoacetate and 0.7 g of potassium carbonate were stirred in 10 ml of dimethylformamide at 60° C. for 4 hours. The reaction mixture was poured in water and extracted with ethyl acetate, and the extract was dried over anhydrous sodium sulfate and, after the removal of the solvent, purified using silica gel chromatography to obtain 1.19 g of methoxycarbonylmethyl 3,6-dichloro-2-( 4,6-dimethoxy-2-pyrimidyl-)methyloxy]benzoate (yield 85%).

Compound Nos. 38, 40, 42, 69, 70 and 71 shown in the above Table 1 were synthesized in the same manner as described above, changing raw materials for reaction.

The NMR spectra and/or melting points of these compounds are shown in Table 3. In the table, "—" means "unmeasured".

TABLE 3

| Compound No. | ¹H-NMR (δ, in CDCl₃ ; ppm) | M.P. (°C.) |
|---|---|---|
| 38 | — | — |
| 40 | — | — |
| 41 | 3.75(3H, s), 3.90(6H, s), 4.78(2H, s) 5.16(2H, s), 5.94(1H, s), 7.12(1H, d), 7.40(1H, d) | — |
| 42 | — | — |
| 69 | 1.27(3H, t), 1.27(3H, d), 3.92(6H, s), 4.23(2H, q), 5.19(2H, s), 5.27 (1H, q), 5.79(1H, s), 6.97–7.97(3H, m) | — |
| 70 | — | — |
| 71 | 3.75(3H, s), 3.90(6H, s), 4.78(2H, s), 5.16(2H, s), 5.94(1H, s), 6.95–7.90(3H, m) | — |

EXAMPLE 3

Synthesis of ethyl 6-chloro-2-[ 4,6-dimethoxy-2-pyrimidyl)methyloxy] benzoate (Compound No. 24) (Process C)

1.0 g of 6-chloro-2-[ (4,6-dimethoxy-2-pyrimidyl)methyloxy] benzoic acid was dissolved in 20 ml of tetrahydrofuran and cooled with ice. 0.35 g of triethylamine dissolved in 1 ml of tetrahydrofuran and 0.40 g of ethyl chloroformate dissolved in 1 ml of tetrahydrofuran were added thereto, and the mixture was stirred under ice cooling for about 30 minutes. Then, a solution of 1 g of ethanol and 0.35 g of triethylamine in 2 ml of tetrahydrofuran was added, and the temperature was raised up to room temperature in about one hour. After the removal of the solvent, the residue was purified using column chromatography to obtain 1.0 g of ethyl 6-chloro-2-[ (4,6-dimethoxy-2-pyrmidyl)methyloxy] benzoate (yield 92%).

The NMR spectrum (¹H-NMR: δ, in CDCl₃; ppm) was 1.26(3H,t), 3.83(6H,s), 4.26(2H,q), 5.13(2H,s), 5.83(1H,s), 6.66–7.40(3H,m) .

EXAMPLE 4

Synthesis of 2-[ (4,6-dimethoxy-2-pyrimidyl)methyloxy]benzoic acid (Compound No. 1) (Process D)

1.5 g of methyl 2-[(4,6-dimethoxy-2-pyrimidyl)methyloxy] benzoate was dissolved in 10 ml of ethanol. 10 ml of water and then 7 ml of 1N aqueous potassium hydroxide solution were added to this solution, and the mixture was stirred until it got to be clear (about 4 hours). The reaction solution was diluted with water and washed with ether, the water layer was neutralized with 1N hydrochloric acid and extracted with chloroform, the extract was dried over anhydrous magnesium sulfate, and the solvent was distilled off to obtain 1.3 g of 2-[ (4,6-dimethoxy-2-pyrimidyl)methyloxy] benzoic acid (yield 91%).

The NMR spectrum (¹H-NMR: δ, CDCl₃; ppm) of this compound was 3.9(3H,s), 5.23(2H,s), 5.93(1H,s), 6.8–7.9 (4H,m).

EXAMPLE 5

Synthesis of 6-chloro-2-[ (4,6-dimethoxy-2-pyrimidyl)methyloxy] benzoic acid (Compound No. 22) (Process D)

3.8 g of ethoxymethyl 6-chloro-2-[ (4,6-dimethoxy- 2-pyrimidyl)methyloxy]benzoate was stirred in a mixed solvent of 30 ml of methanol and 10 ml of water, 0.5 ml of concentrated hydrochloric acid was added, and the mixture was subjected to reaction at room temperature for about 2 hours. The reaction solution was diluted with water and extracted with chloroform, the extract was dried over anhydrous sodium sulfate, and the solvent was distilled off to obtain 3.1 g of 6-chloro-2-[(4,6-dimethoxy- 2-pyrimidyl)methyloxy]benzoic acid (yield 95%).

Compound Nos. 6, 11, 16, 36, 44, 49 and 60 shown in the above Table 1 were synthesized in the same manner as described above, changing raw materials for reaction.

The NMR spectra and/or melting points of these compounds are shown in Table 4. In the table, "—" means "unmeasured".

TABLE 4

| Compound No. | ¹H-NMR (δ, in CDCl₃ ; ppm) | M.P. (°C.) |
|---|---|---|
| 6 | — | 129–130 |
| 11 | — | 180–182 |
| 16 | — | 195–200 |
| 22 | 3.85(6H, s), 5.13(2H, s), 5.93(1H, s), 6.7–7.3(3H, m) | 165–167 |
| 36 | 3.90(6H, s), 5.13(2H, s), 5.98(1H, s), 7.16(1H, d), 7.41(1H, d) | — |
| 44 | 2.56(3H, s), 2.92(6H, s), 5.33(2H, s), 5.96(1H, s), 6.80–7.33(3H, m) | — |
| 49 | 3.76(3H, s), 3.83(6H, s), 5.08(2H, s), 6.01(1H, s), 6.16–6.73(2H, m), 7.03–7.2(1H, m) | — |
| 60 | — | 232–234 |

EXAMPLE 6

Synthesis of the diethylamine salt of 6-chloro-2-(4,6-dimethoxy-2-pyrimidyl)methyloxy]benzoic acid (Compound No. 75) (Process E)

0.4 g of 6-chloro-2-[(4,6-dimethoxy-2-pyrimidyl)methyloxy] benzoic acid was dissolved in 5 ml of tetrahydrofuran, 0.11 g of diethylamine was added to this solution, the mixture was stirred, and the solvent was distilled off under reduced pressure to obtain 0.49 g of the diethylamine salt of 6-chloro-2-[(4,6-dimethoxy-2-pyrimidyl)methoxy] benzoic acid.

Compound Nos. 33, 54, 73, 74 and 75 shown in the above Table 1 were synthesized in the same manner as described above, changing raw materials for reaction.

The NMR spectra and/or melting points of these compounds are shown in Table 5. In the table, "—" means "unmeasured".

TABLE 5

| Compound No. | ¹H-NMR (δ, in CDCl₃; ppm) | M.P. (°C.) |
|---|---|---|
| 33 | — | 192–195 (de-composed) |
| 54 | 1.30(9H, t), 3.05(6H, q), 3.90(3H, s), 5.10(2H, s), 5.94(1H, s), 6.95–7.90(3H, m) | — |
| 73 | — | — |
| 74 | — | — |
| 75 | 1.30(6H, t), 2.83(4H, q), 3.86(6H, s), 5.07(2H, s), 5.90(1H, s), 6.80–7.30(3H, m) | — |

It was found as a result of the research of the present inventors that the above compounds (1) of this invention have an excellent weed killing activity against various weeds and high safety on cultivation crops.

Thus by this invention, a herbicide is provided comprising an aforesaid compound (1) and agriculturally acceptable carriers.

The herbicide of this invention contains as the effective ingredient a novel phenoxymethylpyrimidine derivative of the above general formula (1).

When a compound of this invention represented by the above general formula (1) is used as a herbicide, it can be mixed with solid or liquid carriers or diluents agriculturally known per se, and a surfactant and other auxiliaries for formulation, by a method known per se, and formulated into a preparation form usually used for pesticides, for example, a granule, an emulsion, a wettable powder, a flowable agent or the like. Further, it is possible to use it in mixing with other pesticides, for example, a disinfectant, an insecticide, a miticide, another herbicide, plant growth regulators, fertilizers soil conditioners, etc. Particularly by use thereof in mixing with another herbicide, it is not only possible to decrease the use amount of the chemical and simplify the work, but also possible to expect the enlargement of the weed killing spectrum due to the synergism of both chemicals and a still higher effect due to the synergism.

As solid carriers usable for the above formulation, there can be exemplified clays represented by kaolinites, montmorillonites, illites, polygroskites, etc., specifically pyrophillite, atapulgite, sepiolite, kaolinite, bentonite, saponite, vermiculite, mica, talc, etc.; other inorganic substances such as gypsum, calcium carbonate, dolomite, diatom earth, calcite, magnesium lime, phosphorus lime, zeolite, silicic anhydride and synthetic calcium silicate; vegetable organic substances such as soybean meal, tobacco meal, walnut meal, wheat flour, wood meal, starch and crystalline cellulose; synthetic or natural high molecular compounds such as cumarone resins, petroleum resins, alkyd resins, polyvinyl chloride, polyalkylene glycols, ketone resins, ester gums, copal gum and dammar gum; waxes such as carnauba wax and beeswax; urea; etc.

As suitable liquid carriers, there can, for example, be mentioned paraffinic or naphthenic hydrocarbons such as kerosene, mineral oil, spindle oil and white oil; aromatic hydrocarbons such as xylene, ethylbenzene, cumene and methylnaphthalene; chlorinated hydrocarbons such as trichloroethylene, monochlorobenzene and o-chlorotluene; ethers such as dioxane and tetrahydrofuran; ketones such as methyl ethyl ketone, diisobutyl ketone, dichlorohexanone, acetophenone and isophorone; esters such as ethyl acetate, amyl acetate, ethylene glycol acetate, diethylene glycol acetate, dibutyl maleate and diethyl succinate; alcohols such as n-hexanol, ethylene glycol, diethylene glycol, cyclohexanol and benzyl alcohol; ether alcohols such as ethylene glycol ethyl ether, ethylene glycol phenyl ether, diethylene glycol ethyl ether and diethylene glycol butyl ether; polar solvents such as dimethylformamide and dimethylsulfoxide; water; etc.

In addition, it is also possible to use surfactants and other auxiliaries for the purpose of the emulsification, dispersion, wetting, diffusion and spreading, bond and disintegrability adjustment of the effective ingredient; the stabilization of the effective ingredient; fluidity improvement; rust prevention; etc. As surfactants, there can be used any of nonionic, anionic, cationic and amphoteric surfactants, but usually used are nonionic and (or) anionic surfactants.

As suitable nonionic surfactants, there can, for example, be mentioned a compound obtained by the addition of ethylene oxide to a higher alcohol such as lauryl alcohol, stearyl alcohol or oleyl alcohol through polymerization; a compound obtained by the addition of ethylene oxide to an alkylphenol such as isooctylphenol or nonylphenol through polymerization; a compound obtained by the addition of ethylene oxide to an alkylnaphthol such as butylnaphthol or octylnaphthol through polymerization; a compound obtained by the addition of ethylene oxide to a higher fatty acid such as palmitic acid, stearic acid or oleic acid through polymerization; a compound obtained by the addition of ethylene oxide to an amine such as dodecylamine or stearamide through polymerization; a higher fatty acid ester of a polyhydric alcohol such as sorbitan or a compound obtained by the addition of ethylene oxide thereto through polymerization; a compound obtained by the addition of ethylene oxide to propylene oxide through block polymerization, etc.

As suitable anionic surfactants, there can, for example, be mentioned alkyl sulfate ester salts such as sodium lauryl sulfate and oleyl alcohol sulfate ester amine salts; alkylsulfonate salts such as sodium dioctyl sulfosuccinate and sodium 2-ethylhexenesulfonate; arylsulfonate salts such as sodium isopropylnaphthalenesulfonate, sodium methylenebisnaphthalenesulfonate, sodium ligninsulfonate and sodium dodecylbenzenesulfonate; etc.

Further, for the purpose of the improvement of the performance of the preparation and the enhancement of the herbicidal effect, it is also possible to use together therewith a high molecular compound such as casein, gelatin, albumin, glue, a ligninsulfonate salt, an alginate salt, gum arabic, carboxymethylcellulose, methylcellulose, hydroxyethylcellulose, polyvinylaldol, polyvinylpyrrolidone or a polysaccharide; and other auxiliaries.

The above carriers and various auxiliaries can appropriately by used alone or in combination according to the purpose, taking the form, application site, etc. of the preparation into amount.

The effective ingredient content of the compound of this invention in the thus obtainable various preparation forms can variously be changed according to the forms, but it is suitable that it is usually 0.1 to 99 wt. %, preferably 1 to 80 wt. %.

In the case of wettable powder, it contains, for example, usually 25 to 90 wt. % of the effective ingredient, and the residual part comprises solid carriers and a dispersing and wetting agent, and, if necessary, a protective colloid agent, an antifoaming agent, etc. are added.

In the case of granules, they contain, for example, usually 1 to 35 wt. % of the effective ingredient, and the residual part comprises solid carriers, a surfactant, etc. The effective ingredient is either uniformly mixed with the solid carriers or uniformly stuck or adsorbed on the surface of the solid carriers, and the diameter of the granules is on the order of about 0.2 to 1.5 mm.

In the case of a flowable agent, it contains, for example, usually 5 to 50 wt. % of the effective ingredient, and 3 to 10 wt. % of a dispersing and wetting agent is contained therein and the residual part is water, and, if necessary, a protective colloid agent, an antiseptic, an antifoaming agent, etc. are added.

A novel methylphenoxypyrimidine derivative of this invention can be applied either as a compound of the above general formula (1) itself or in any preparation form mentioned above.

The herbicide of this invention can be applied to various weeds from before the occurrence to the growth stage growing in paddy fields or fields. Its application amount is suitably on the order of 0.01 to 10 kg, preferably 0.1 to 1 kg per hectare as the amount of the compound represented by the above general formula (1) (effective ingredient amount), and can appropriately be chosen or altered depending on the kind and growth stage of the target weeds, application places, application time, weather, etc.

Several embodiments of herbicides containing compounds of this invention are described below according to preparation examples.

"Parts" in the following examples are based on weight.

Sodium ligninsulfonate 2 parts

Polyoxyethylene alkylaryl ether 1 part

The above substances were sufficiently mixed, a suitable amount of water was added, and the mixture was kneaded and granuled using an extruder for granulation to obtain 100 parts of granules.

| Preparation example 2 (wettable powder) | |
|---|---|
| Compound No. 32 | 20 parts |
| Diatom earth | 73 parts |
| Calcium ligninsulfonate | 5 parts |
| Alkylnaphthalenesulfonic acid-formalin condensate | 2 parts |

The above substances were mixed and ground by a jet mill to obtain 100 parts of a wettable powder.

| Preparation example 3 (emulsion) | |
|---|---|
| Compound No. 57 | 30 parts |
| Xylene | 55 parts |
| Cyclohexanone | 10 parts |
| Calcium dodecylbenzenesulfonate | 3 parts |
| Polyoxyethylene alkylaryl ether | 2 parts |

The above substances were uninformly mixed to obtain 100 parts of an emulsion.

| Preparation example 4 (flowable agent) | |
|---|---|
| Compound No. 22 | 30 parts |
| Sodium di-2-ethylhexyl sulfosuccinate | 2 parts |
| Polyoxyethylene nonylpnenyl ether | 3 parts |
| Antifoaming agent | 1 part |
| Propylene glycol | 5 parts |
| Water | 59 parts |

The above substances were uniformly ground and mixed by a wet type ball mill to obtain 100 parts of a flowable agent.

Herbicides containing compounds of this invention can be prepared according to the above examples.

EFFECT OF THE INVENTION

The phenoxymethylpyrimidine derivatives of this invention represented by the above general formula (1) are novel compounds not disclosed in literatures. The characteristic of the compounds of this invention represented by the above general formula (1) is to take structure such that the phenyl group and the 2-position of the 4,6-di-lower alkoxypyrimidine bind through an oxygen atom and a methylene group, and it is surmised that an excellent herbicidal action is exerted due to the structural characteristic.

The compounds of this invention represented by the above general formula (1) have an extremely high herbicidal effect, and have wide weed killing spectra at a low amount thereof and on the other hand exhibit excellent safety on cultivation crops, and therefore can be an agriculturally useful herbicide.

The compounds and herbicide of this invention can effectively control various weeds growing on paddy fields or fields over a wide term from before the occurrence to the growth stage. For example, it is possible to control thereby annual weeds occurring on paddy fields such as barnyard glass, tamagayatsuri, konagi, azena, kikashigusa and mizohakobe; and perennial weeds occuring on paddy fields such as matsubai, hotarui, heraomodaka, urikawa, mizugayatsuri, arrowhead, hirumushiro, pistil, koukiyagara, dropwort, ezonosayanukagusa and kusanemu.

Further, they exhibit a remarkable effect not only annual weeds occurring on fields such as Deccan glass, crabgrass, wire grass, foxtail, suzumenoteppo, chickweed, polygonums, Deccan grasses, Indian mallow, shiroza, American kingojika, cocklebur, ragweed, shepherd's purse, lady's-smock, Spanish needles, cleavers and black bindweed, but perennial weeds occurring on fields such as nut grass, convolvulus, Jonson grass and shibamugi.

Further, the compounds and herbicide of this invention can effectively control annual and perennial weeds occurring not only on paddy fields or fields, but on agricultural lands such as orchards and mulberry fields or on non-agricultural lands such as lawns and ridges between rice fields.

Moreover, the compounds of this invention have high safety on cultivation crops, and do not give phytotoxicity, in such a degree that it comes into a practical problem, against the growth of, particularly, useful Gramineae crops such as rice plant, corn, wheat and barley, and useful broadleaf crops such as soybean and cotton.

The effect of the herbicide of this invention is described below according to test examples.

Test example 1 (treatment of paddy field soil)

Paddy field soil mixed with an appropriate amount of a compound fertilizer was packed in a plastic pot having an area of 170 cm$^2$, and one root (two stems per one root) of a paddy rice plant (breed: Koshihikari) of the two-leaf stage grown in advance in a greenhouse was transplanted thereon and further seeds of barnyard glass, konagi, azena and hotarui were sown.

Three days after the transplantation of the paddy rice plant and the sowing of the weeds, each compound shown in Table 6 was made into a wettable powder in the same manner as in Preparation example 2, the wettable powder was suspended in water, and the suspension was added dropwise with a pipet in an amount of 1.0 kg or 5.0 kg of the effective ingredient per ha.

A herbicidal effect and the degree of phytotoxicity were investigated 30 days after the chemical treatment based on the following criterion.

The results are shown in Table 6.

Phytotoxicity which substantially comes into a problem on the growth of the paddy rice plant was not observed about any of the compounds.

| Grade | Herbicidal effect Weed killing percentage based on the untreated area (%) | Phytotoxicity degree Phytotoxicity percentage based on the untreated area (%) |
|---|---|---|
| 0 | 0 | |
| 1 | above 0, 10 or less | |
| 2 | above 10, 20 or less | |
| 3 | above 20, 30 or less | |
| 4 | above 30, 40 or less | the same as left |
| 5 | above 40, 50 or less | |
| 6 | above 50, 60 or less | |
| 7 | above 60, 70 or less | |
| 8 | above 70, 80 or less | |
| 9 | above 80, 90 or less | |
| 10 | above 90, 100 or less | |

TABLE 6

| Compound No. | Effective ingredient amount kg/ha | Barnyard glass | Hotarui | Konagil | Azena |
|---|---|---|---|---|---|
| 22 | 1 | 10 | 10 | 10 | 10 |
|  | 5 | 10 | 10 | 10 | 10 |
| 24 | 1 | 10 | 10 | 10 | 10 |
|  | 5 | 10 | 10 | 10 | 10 |
| 32 | 1 | 10 | 10 | 10 | 10 |
|  | 5 | 10 | 10 | 10 | 10 |
| 33 | 1 | 10 | 10 | 10 | 10 |
|  | 5 | 10 | 10 | 10 | 10 |
| 44 | 1 | 10 | 10 | 10 | 10 |
|  | 5 | 10 | 10 | 10 | 10 |
| 49 | 1 | 10 | 10 | 10 | 10 |
|  | 5 | 10 | 10 | 10 | 10 |
| 54 | 1 | 10 | 10 | 10 | 10 |
|  | 5 | 10 | 10 | 10 | 10 |
| 73 | 1 | 10 | 10 | 10 | 10 |
|  | 5 | 10 | 10 | 10 | 10 |
| 74 | 1 | 10 | 10 | 10 | 10 |
|  | 5 | 10 | 10 | 10 | 10 |
| 75 | 1 | 10 | 10 | 10 | 10 |
|  | 5 | 10 | 10 | 10 | 10 |

Test example 2 (treatment at growth stage in paddy field)

Paddy field soil mixed with an appropriate amount of a compound fertilizer was packed in a plastic pot having an area of 170 cm$^2$, and one roof (two stems per one root) of a paddy rice plant (breed: Koshihikari) of the two-leaf stage grown in advance in a greenhouse was transplanted thereon and further seeds of barnyard grass, konagi, azena and hotarui were sown.

Ten days after the transplantation of the paddy rice plant and the sowing of the weeds and at the 1.5-leaf stage of the barnyard glass, each compound shown in Table 7 was made into a wettable powder in the same manner as in Preparation example 2, the wettable powder was suspended in water, and the suspension was added dropwise with a pipet in an amount of 1.0 kg or 5.0 kg of the effective ingredient per ha.

A herbicidal effect and the degree of phytotoxicity were investigated 30 days after the chemical treatment based on the assessment criterion shown in Test example 1.

The results are shown in Table 7.

Phytotoxicity which substantially comes into a problem on the growth of the paddy rice plant was not observed about any of the compounds.

TABLE 7

| Compound No. | Effective ingredient amount kg/ha | Barnyard glass | Hotarui | Konagil | Azena |
|---|---|---|---|---|---|
| 22 | 1 | 10 | — | 10 | 10 |
|  | 5 | 10 | 10 | 10 | 10 |
| 24 | 1 | 10 | 9 | 10 | 10 |
|  | 5 | 10 | 10 | 10 | 10 |
| 32 | 1 | 10 | 10 | 10 | 10 |
|  | 5 | 10 | 10 | 10 | 10 |
| 33 | 1 | 10 | — | 10 | 10 |
|  | 5 | 10 | 10 | 10 | 10 |
| 44 | 1 | 10 | 10 | 10 | 10 |
|  | 5 | 10 | 10 | 10 | 10 |
| 49 | 1 | 10 | — | 10 | 10 |
|  | 5 | 10 | 10 | 10 | 10 |
| 54 | 1 | 10 | — | 10 | 10 |
|  | 5 | 10 | 10 | 10 | 10 |
| 73 | 1 | 10 | 10 | 10 | 10 |
|  | 5 | 10 | 10 | 10 | 10 |
| 74 | 1 | 10 | 9 | 10 | 10 |
|  | 5 | 10 | 10 | 10 | 10 |
| 75 | 1 | 10 | 10 | 10 | 10 |
|  | 5 | 10 | 10 | 10 | 10 |

Test example 3 (treatment before germination in field)

Field soil mixed with an appropriate amount of a compound fertilizer was packed in a plastic pot having an area of 170 cm$^2$, and seeds were sown of wheat, barnyard glass, crabgrass, aobiyu, Indian mallow, oinutade, cocklebur and shirobanachosenasagao.

One day after the sowing, each compound shown in Table 8 was made into a wettable powder in the same manner as in Preparation example 2, the wettable powder was diluted with an appropriate amount of water, and the resultant dilution was uniformly sprayed on the soil surface through a glass nozzle so that the spray amount got to be 1.0 kg or 5.0 kg per ha in terms of the effective ingredient. A herbicidal effect and the degree of phytotoxicity were investigated 30 days after the chemical treatment based on the assessment criterion shown in Test example 1.

The results are shown in Table 8.

TABLE 8

| Compound No. | Effective ingredient amount kg/ha | Barnyard grass | Crabgrass | Aobiyu | Indian mallow | Cocklebur | Polygonum | Shirobanacho-senasagao | Phytotoxicity degree Wheat |
|---|---|---|---|---|---|---|---|---|---|
| 22 | 1 | — | 9 | 10 | 10 | 10 | 10 | 10 | 0 |
|  | 5 | 10 | 10 | 10 | 10 | 10 | 10 | 10 | 2 |
| 24 | 1 | 9 | 9 | 10 | 10 | 10 | 10 | 10 | 0 |
|  | 5 | 10 | 10 | 10 | 10 | 10 | 10 | 10 | 2 |
| 32 | 1 | — | 9 | 10 | 10 | 10 | 10 | 10 | 0 |
|  | 5 | 10 | 10 | 10 | 10 | 10 | 10 | 10 | 2 |

TABLE 8-continued

| Compound No. | Effective ingredient amount kg/ha | Herbicidal effect | | | | | | | Phytotoxicity degree Wheat |
|---|---|---|---|---|---|---|---|---|---|
| | | Barnyard grass | Crabgrass | Aobiyu | Indian mallow | Cocklebur | Polygonum | Shirobanacho-senasagao | |
| 33 | 1 | — | 9 | 10 | 10 | 10 | 10 | 10 | 0 |
| | 5 | 10 | 10 | 10 | 10 | 10 | 10 | 10 | 2 |
| 44 | 1 | 10 | 10 | 10 | 10 | 10 | 10 | 10 | 0 |
| | 5 | 10 | 10 | 10 | 10 | 10 | 10 | 10 | 1 |
| 49 | 1 | 10 | 10 | 10 | 10 | 10 | 10 | 10 | 0 |
| | 5 | 10 | 10 | 10 | 10 | 10 | 10 | 10 | 1 |
| 54 | 1 | 9 | 9 | 10 | 10 | 10 | 10 | 10 | 0 |
| | 5 | 10 | 10 | 10 | 10 | 10 | 10 | 10 | 2 |
| 73 | 1 | 9 | 10 | 10 | 10 | 10 | 10 | 10 | 0 |
| | 5 | 10 | 10 | 10 | 10 | 10 | 10 | 10 | 2 |
| 74 | 1 | 10 | 9 | 10 | 10 | 10 | 10 | 10 | 0 |
| | 5 | 10 | 10 | 10 | 10 | 10 | 10 | 10 | 2 |
| 75 | 1 | 10 | 10 | 10 | 10 | 10 | 10 | 10 | 0 |
| | 5 | 10 | 10 | 10 | 10 | 10 | 10 | 10 | 2 |

Text example 4 (treatment at the growth stage in field)

Field soil mixed with an appropriate amount of a compound fertilizer was packed in a plastic pot having an area of 170 cm$^2$, and seeds were sown of wheat, barnyard grass, crabgrass, akinoenokorogusa, aobiyu, Indian mallow, oinutade, cocklebur and shirobana-chosenasagao.

15 days after the sowing, each compound shown in Table 9 was made into a wettable powder in the same manner as in Preparation example 2, the wettable powder was diluted with an appropriate amount of water, and Surfactant WK (a surfactant produced by Maruwa Biochemical Co., Ltd.) was added to a final concentration of 0.25%. The resultant suspension was uniformly sprayed on the stems and leaves of the plants so that the spray amount got to be 1.0 kg or 5.0 kg per ha in terms of the effective ingredient. A herbicidal effect and the degree of phytotoxicity were investigated 30 days after the chemical treatment based on the assessment criterion shown in Test example 1.

The results are shown in Table 9.

Test example 5 (field test)

In an outdoor field, seeds of wheat (breed: Shirane) were sown in many rows with appropriate mutual intervals and seeds of weeds shown in Table 10 were mixed with the surface layer of the soil, and the whole area was divided into test areas each of 2 m×4 m.

20 days after the sowing, each compound shown in Table 10 was made into a wettable powder in the same manner as in Preparation example 2, the wettable powder was diluted with an appropriate amount of water, and Surfactant WK (a surfactant produced by Maruwa Biochemical Co., Ltd.) was added to a final concentration of 0.2%. The resultant suspension was uniformly sprayed in an amount of 500 ml per test area which corresponds to 50 g or 100 g of the effective ingredient per ha.

50 days after the chemical treatment, the herbicidal effect on each weed and the phytotoxicity degree on the wheat were judged according to the assessment criterion shown in Test example 1.

TABLE 9

| Compound No. | Effective ingredient amount kg/ha | Herbicidal effect | | | | | | | | Phytotoxicity degree Wheat |
|---|---|---|---|---|---|---|---|---|---|---|
| | | Barnyard grass | Crabgrass | Akinoeno-korogusa | Aobiyu | Indian mallow | Cocklebur | Polygonum | Shirobanacho-senasagao | |
| 22 | 1 | — | — | — | 10 | 10 | 10 | 10 | 10 | 0 |
| | 5 | 10 | 10 | 10 | 10 | 10 | 10 | 10 | 10 | 2 |
| 24 | 1 | 10 | 9 | — | 10 | 10 | 10 | 10 | 10 | 0 |
| | 5 | 10 | 10 | 10 | 10 | 10 | 10 | 10 | 10 | 2 |
| 32 | 1 | 10 | 9 | — | 10 | 10 | 10 | 10 | 10 | 0 |
| | 5 | 10 | 10 | 10 | 10 | 10 | 10 | 10 | 10 | 2 |
| 33 | 1 | 10 | 9 | — | 10 | 10 | 10 | 10 | 10 | 0 |
| | 5 | 10 | 10 | 10 | 10 | 10 | 10 | 10 | 10 | 2 |
| 44 | 1 | 10 | — | — | 10 | 10 | 10 | 10 | 10 | 0 |
| | 5 | 10 | 10 | 10 | 10 | 10 | 10 | 10 | 10 | 1 |
| 49 | 1 | 9 | 9 | 10 | 10 | 10 | 10 | 10 | 10 | 0 |
| | 5 | 10 | 10 | 10 | 10 | 10 | 10 | 10 | 10 | 1 |
| 54 | 1 | 10 | 9 | — | 10 | 10 | 10 | 10 | 10 | 0 |
| | 5 | 10 | 10 | 10 | 10 | 10 | 10 | 10 | 10 | 2 |
| 73 | 1 | 10 | 10 | 9 | 10 | 10 | 10 | 10 | 10 | 0 |
| | 5 | 10 | 10 | 10 | 10 | 10 | 10 | 10 | 10 | 2 |
| 74 | 1 | 10 | 10 | 9 | 10 | 10 | 10 | 10 | 10 | 0 |
| | 5 | 10 | 10 | 10 | 10 | 10 | 10 | 10 | 10 | 2 |
| 75 | 1 | 10 | 10 | 10 | 10 | 10 | 10 | 10 | 10 | 0 |
| | 5 | 10 | 10 | 10 | 10 | 10 | 10 | 10 | 10 | 2 |

The results are shown in Table 10.

TABLE 10

| Compound No. | Effective ingredient amount g/ha | Herbicidal effect | | | Phytotoxicity degree Wheat |
|---|---|---|---|---|---|
| | | Cleavers | Chickweed | Shepherd's purse | |
| 22 | 50 | 10 | 10 | 10 | 0 |
| | 100 | 10 | 10 | 10 | 0 |
| 75 | 50 | 10 | 10 | 10 | 0 |
| | 100 | 10 | 10 | 10 | 0 |
| 54 | 50 | 10 | 10 | 10 | 0 |
| | 100 | 10 | 10 | 10 | 0 |
| 33 | 50 | 10 | 10 | 10 | 0 |
| | 100 | 10 | 10 | 10 | 0 |
| 32 | 50 | 10 | 10 | 10 | 0 |
| | 100 | 10 | 10 | 10 | 0 |

We claim:

1. A phenoxymethylpyrimidine derivative represented by the following formula (1)

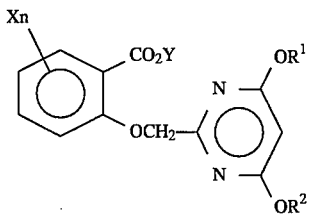

wherein

X is a halogen atom, a lower alkyl group, a lower alkoxy group, a lower acyloxy group or a nitro group, n is an integer of 0, 1, 2, Y is a hydrogen atom, a lower alkyl group, a lower alkenyl group, a lower alkynyl group, a lower alkyl group substituted by substituents selected from halogen atoms, lower alkoxy groups, lower alkylthio groups, a carboxyl group, carboxyalkyl groups, a phenyl group, phenyl groups substituted by halogen atom(s), lower alkyl group(s) or lower alkoxy group(s), heterocyclic groups, and heterocyclic groups substituted by halogen atom(s), lower alkyl group(s), lower alkoxy group(s) or lower alkylthio group(s), a lower alkenyl group which is substituted by substituent(s) selected from halogen atoms, lower alkoxy groups, lower alkylthio groups, a carboxyl group, carboxyalkyl groups, a phenyl group, phenyl groups substituted by halogen atom(s), lower alkyl group(s) or lower alkoxy group(s), heterocyclic groups and heterocyclic groups substituted by halogen atom(s), lower alkyl group(s), lower alkoxy group(s) and lower alkylthio group(s), a lower alkynyl group which is substituted by substituent(s) selected from halogen atoms, lower alkoxy groups, lower alkylthio groups, a carboxyl group, carboxyalkyl groups, a phenyl group, phenyl groups substituted by halogen atom(s), lower alkyl group(s) or lower alkoxy group(s), heterocyclic groups and heterocyclic groups substituted by halogen atom(s), lower alkyl group(s), lower alkoxy group(s) and lower alkylthio group(s), an alkali metal atom, an alkaline earth metal atom or an ammonium cation optionally substituted by alkyl group(s), wherein each of the aforementioned heterocyclic groups is selected from the group consisting of pyridyl, thienyl, furyl, pyrimidyl, pyrazolyl, imidazoyl, triazoyl and thiazolyl and $R^1$ and $R^2$ each independently is a lower alkyl group.

2. The phenoxymethylpyrimidine derivative according to claim 1 wherein X is a halogen atom, a lower alkyl group or a lower alkoxy group.

3. The phenoxymethylpyrimidine derivative according to claim 1 wherein X is a chlorine atom, a methyl group or a methoxy group.

4. The phenoxymethylpyrimidine derivative according to claim 1 wherein n is 1.

5. The phenoxymethylpyrimidine derivative according to claim 1 wherein n is 1 and X is located at the 6-position on the benzene ring.

6. The phenoxymethylpyrimidine derivative according to claim 1 wherein Y is a hydrogen atom, a sodium atom, a lower alkyl group of an optionally alkyl-substituted ammonium cation.

7. The phenoxymethylpyrimidine derivative according to claim 1 wherein Y is a hydrogen atom, a methyl group, an ethyl group or an optionally alkyl-substituted ammonium cation.

8. The phenoxymethylpyrimidine derivative according to claim 1 wherein both $R^1$ and $R^2$ are methyl groups.

9. A herbicidal composition comprising an effective amount of a phenoxymethylpyrimidine derivative according to claim 1 and agriculturally acceptable carriers or diluents.

10. A method for the control or weed killing of weeds which comprises applying an effective amount of a phenoxymethylpyridine derivative according to claim 1 in an area where weeds are growing or an area where the growth of weeds is expected.

11. A method for control or weed killing of weeds which comprises applying an effective amount of a phenoxymethylpyridine derivative according to claim 1 in an area where a cultivation crop is cultivated or an area where the cultivation thereof is scheduled.

* * * * *